United States Patent [19]

Tramier et al.

[11] 4,108,866
[45] Aug. 22, 1978

[54] SULPHOXIDES

[75] Inventors: Bernard Tramier, Pau; Raymond Delourme, Billere; Philippe Fresnel, Castres, all of France

[73] Assignee: Societe Nationale des Petroles d'Aquitaine, Courbevoie, France

[21] Appl. No.: 804,638

[22] Filed: Jun. 8, 1977

Related U.S. Application Data

[63] Continuation of Ser. No. 644,718, Dec. 29, 1975, abandoned, which is a continuation of Ser. No. 545,487, Jan. 30, 1975, abandoned.

[51] Int. Cl.$^2$ ............................................. C07D 333/02
[52] U.S. Cl. ............................ 260/329 R; 260/607 E; 260/607 AL; 260/327 R; 260/327 TH; 106/308 Q; 252/544; 252/549; 203/DIG. 6
[58] Field of Search .......... 260/607 E, 327 R, 327 E, 260/327 TH, 329 R, 607 A, 607 AL; 203/95, 96, 67, 70, 69, 60, DIG. 6

[56] References Cited

U.S. PATENT DOCUMENTS 3,773,838  11/1973  Andruski et al. ............... 260/607 A
3,849,499  11/1974  Malievsky ..................... 260/607 A

*Primary Examiner*—Lewis Gotts
*Assistant Examiner*—Molly C. Eakin
*Attorney, Agent, or Firm*—Norman S. Blodgett; Gerry A. Blodgett

[57] ABSTRACT

An improved method of producing dialkyl-sulfoxides by oxidizing corresponding dialkyl-sulfides with hydrogen peroxide in aqueous acidic medium. It remedies the drawback of the similar prior art as concerns the separation of the sulfoxide formed from its reaction medium. The new method permits of easily recovering the sulfoxides in the state of good purity.

The improvement consists in mixing the reaction medium with a large proportion of a solvent capable of yielding an azeotropic mixture with water. Then, after oxidization, the water is removed by distillation as azeotropic mixture. Preferably solvents are used which dissolve the dialkyl-sulfide but do not dissolve the sulfoxide formed; heptane is a particularly useful solvent. When an excess of the solvent is used, there is obtained, after distilling off the azeotropic mixture, a slurry of sulfoxide and solvent, easy to separate.

3 Claims, No Drawings

SULPHOXIDES

This is a continuation, of application Ser. No. 644,718, filed Dec. 29, 1975 now abandoned, which is a continuation of application Ser. No. 545,487 filed Jan. 30, 1975 now abandoned.

Different sulphoxides are finding increasing use at the present time, especially in the form of solvents, as intermediates for the preparation of other compounds, additives to detergent baths and polymerisation emulsions. Their manufacture, therefore, is of interest to industry. The most commonly used known process is based upon the oxidation of the corresponding sulphide with hydrogen peroxide solution and can produce good yields. However, the separation of the sulphoxide from the reaction medium presents difficulties which become particularly troublesome when the sulphoxide is soluble in water. In fact, when the desired product is liquid, it is necessary to recover it from the reaction medium by distillation, which reduces the yield, often to below 70%. Besides this, impurities, such as water and sulphide, are always entrained by the product during distillation, so that it is never completely pure.

On the other hand, when the sulphoxide is solid it is very difficult to recover it by crystallization, since few solvents are capable of extracting such compounds from an aqueous medium. This necessitates the use of large volumes of solvent, and the yield of extract is not satisfactory. For example, in the case of di(hydroxy-2-ethyl) sulphoxide prepared by the oxidation of thiodiglycol with hydrogen peroxide, the yield is not more than 70% and the product is obtained in the form of a paste which must be dried for a long time under vacuum.

These difficulties militate against the large-scale production of certain sulphoxides, more especially those that are soluble in water.

The present invention provides improvement in the preparation of organic sulphoxides, particularly the aliphatic and hydroxyaliphatic sulphoxides. It enables the oxidation of sulphides with hydrogen peroxide to be carried out with greatly increased yields and a considerable improvement in the purity of the final products.

The new process according to the invention, which involves the transformation of the organic sulphide into the corresponding sulphoxide with hydrogen peroxide, is a method of producing a dialkyl-sulphoxide by oxidizing the corresponding dialkyl-sulphide with hydrogen peroxide in a solvent, wherein the solvent is one capable of forming an azeotropic mixture with water and wherein the azeotropic mixture is distilled off from the reaction medium after the oxidation has been effected.

When carrying out the invention, having completed the oxidation, the reaction medium is boiled so as to distil off the azeotrope with the complete elimination of water. Depending on the solubility of the sulphoxide in the solvent employed, the product may remain in solution in the excess solvent or it may precipitate or settle out from suspension. This facilitates its subsequent recovery by precipitation, crystallization, decantation or other means, after the partial or total elimination of the remaining solvent.

Various solvents may be used which include in particular benzene, toluene, hexane, heptane, dichloroethane, chloropropene, propyl acetate and iso-butyl acetate, whose azeotropes contain between 5% and 20% by weight of water.

The new principle, provided by the invention permits the technique for separating the final product to be varied by the choice of the azeotrope-forming solvent. In fact, one can choose a solvent which dissolves both the raw material and the end product, or one in which the sulphide is soluble and the sulphoxide insoluble. An interesting example of the latter is provided by heptane, which dissolves sulphides in the cold but not sulphoxides, facilitating their precipitation at the end of the reaction.

In the new process of the invention, it is not necessary to employ large quantities of acetic acid, if this is used, but a small catalytic proportion is sufficient, and this may be replaced by another organic acid capable of forming peracids by reaction with hydrogen peroxide.

It is understood that the organic solvent, having served to entrain the water in the form of an azeotrope, may be recovered after distillation and separation of the aqueous layer, so that the economy of the new process is not jeopardized by its use.

As indicated above, an important new application of certain sulphoxides is their use as thickening agents in various compositions, especially oil-based products, paints and cosmetics. In this last field, the sulphoxide acts the part of a thickener in formulations based upon the surface active agents of either the anionic, cationic, nonionic or amphoteric type. Although a large number of sulphoxides are suitable for these diverse applications, aliphatic sulphoxides containing two $C_1$-$C_{18}$ alkyl groups, which may be the same or different, are particularly useful and the alkyl groups may carry hydroxyls or form a polymethylene ring.

The sulphides used in carrying out the method according to the invention have the formula $R^1$—S—$R^2$ where $R^1$ and $R^2$, which may be the same or different, are preferably selected from alkyls and hydroxy-alkyls having 1 to 18 carbon atoms. More especially, one or both of the groups $R^1$ and $R^2$ are preferably $C_1$ to $C_4$ alkyls or hydroxy-alkyls.

In the preparation of particularly useful sulphoxides, sulphides are used in which $R^1$ is an alkyl or hydroxy-alkyl having 1 to 3 carbon atoms, while $R^2$ is a $C_6$ to $C_{12}$ alkyl.

Another kind of sulphoxide can be prepared starting from sulphides of the formula

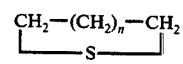

in which $n$ is 0, 1, 2, 3, or 4, preferably 1 or 2.

One particularly advantageous process according to the invention comprises dissolving 1 mole of a dialkyl-sulphide as above defined in about 700 to 1400 ml of heptane, adding to the solution a catalytical amount of an acid, for instance 5 to 20 ml of pure acetic acid and/or 5 to 20 ml of an N/10 aqueous solution of perchloric acid, and substantially 1 mole of $H_2O_2$, heating the mixture until the boiling temperature of the azeotropic heptane-water mixture is reached, allowing the azeotropic mixture to distil off, and then separating the sulphoxide thus formed from the remaining dry heptane.

The $H_2O_2$ is preferably used in form of its commercial aqueous solution containing about 30 to 35% of $H_2O_2$.

The invention is illustrated in the following Examples, which show the preparation of 10 different sulphoxides, as well as some of their applications.

EXAMPLES 1-10

To one mole of organic sulphide, whose composition is indicated in the following Table for each Example, there were added 10 ml of acetic acid, 10 ml of a 0.1N aqueous solution of perchloric acid and 700 ml of heptane. To the sulphide solution thus obtained, 100 ml of 110 vol. hydrogen peroxide were added.

The mixture was heated gently to initiate the reaction, after which the temperature was raised so as to cause the distillation of the heptane/water azeotrope (79.2° C).

When all of the water had been eliminated, the mixture was cooled and the appropriate separation procedure for the sulphoxide product was applied. In Examples 1 - 4, in which the sulphoxide formed was liquid, it was separated from the reaction medium by decantation to obtain a clean product which, on subsequent rectification gave a sulphoxide of high purity.

The sulphoxides of Examples 5 - 7 are solids which precipitate in the reaction medium after the distillation of the azeotrope, and it was sufficient to separate them by filtering or centrifuging and drying. The products obtained were very clean and are free from sulphones.

| Example No. | Raw Material Sulphide of: | Product Obtained | State | Yield |
|---|---|---|---|---|
| 1 | tetra-methylene | Tetramethylene sulphoxide 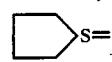 | Liquid | 96. |
| 2 | methyl, hydroxy-2-ethyl | Methyl, hydroxy-2-ethyl sulphoxide $CH_3SOCH_2CH_2OH$ | " | 92.5 |
| 3 | Dipropyl | Dipropyl sulphoxide $CH_3CH_2CH_2SOCH_2CH_2CH_3$ | " | 98. |
| 4 | Di-iso-propyl | Di-isopropyl sulphoxide 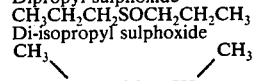 | " | 98. |
| 5 | Methyl,decyl | Methyl, decyl sulphoxide $C_{10}H_{21}SOCH_3$ | Solid | 92. |
| 6 | Hydroxy-2-ethyl, decyl | Hydroxy-2-ethyl, decyl sulphoxide | " | 97. |
| 7 | Di(hydroxy-2-ethyl) | Di(hydroxy-2-ethyl) sulphoxide $HOCH_2CH_2SOCH_2CH_2OH$ | " | 100. |
| 8 | Diethyl | Diethyl sulphoxide | Liquid | 81. |
| 9 | Dimethyl | Dimethyl sulphoxide | " | 87. |
| 10 | Hydroxy-2-ethyl, heptyl | Hydroxy-2-ethyl, heptyl sulphoxide | Solid | 87. |

The sulphoxides prepared as indicated above are of high purity, do not contain sulphide or other irritant substances, and are generally free from sulphones. On account of these qualities, as well as certain unexpected properties, they are suitable for the preparation of various compositions, especially cosmetics. It has been shown, and this forms part of the present invention, that the addition of aliphatic sulphoxides to preparations such as shampoos, foam baths, shaving creams and cosmetic emulsions, e.g. creams and milks, gives rise to a marked increase in viscosity. The sulphoxides are therefore used, according to the invention, in the form of thickeners for diverse cosmetic compositions. The thickening effect is very desirable for the storage of this type of product.

The remarkable property indicated above, of increasing the viscosity, is illustrated in the following Example, in which a conventional shampoo based upon sodium lauryl ether sulphate at a concentration in water of about 30% by weight was tested. This viscosity of the shampoo was measured in the presence of its usual additive, i.e. an alkanol amide lather booster at a concentration of 1%, 3% and 5% by weight. Secondly the same shampoo was examined without additive and, thirdly, the measurement of viscosity was carried out with similar sodium lauryl ether sulphate compositions containing 1%, 3% and 5% of certain sulphoxides, without any other additive.

| Additive-quantity | Viscosity in Centipoises | | | |
|---|---|---|---|---|
| | 0% | 1% | 3% | 5% |
| None | 1.962 | — | — | — |
| Commercial Alkanolanide | — | 1.767 | 2.090 | 3.558 |
| Methyl-dodecyl sulphoxide | — | 2.307 | 5.785 | >1.000 |
| Dodecyl-hydroxy-2-ethyl sulphoxide | — | 1.981 | 3.540 | 480 |
| Methyl-decyl sulphoxide | — | 1.785 | 2.796 | 54.27 |

The results of these experiments are tabulated above:

It can be seen from the figures in the above Table that the increase in viscosity becomes very noticeable with a sulphoxide content of about 3% and is considerable with a content of 5%.

EXAMPLE 11

Preparation of low-viscosity foaming composition

The composition was formed by the following constituents in the proportions by weight indicated:
35 parts of oxyethylated lauryl alcohol mono-sulphosuccinate
15 parts of fatty acid amides of alkyl betaine
25 parts of 28% aqueous solution of sodium lauryl ether sulphate
3 parts of glycol poyether
2 parts methyl - decyl sulphoxide
Water to 100 parts by weight.

This composition differs from similar known products in that methyl decyl sulphoxide replaces the alkanolamide commonly used.

The pH of the above composition was 6.6, its viscosity about 1,000 CP and the active matter content was about 26% by weight.

In a variation of the above composition the usual alkyl betaine was replaced by (dodecyl-hydrocyethyl)- sulphonio-1-sulpho-3 propane, which improved the foaming power.

EXAMPLE 12

High Viscosity foaming composition

The composition comprised:
70 parts by weight of fatty acid amides of alkyl betaine
3 parts by weight of trioxyethylated C12-14 alcohol
3 parts by weight of methyl dodecyl sulphoxide
Water to 100 parts by weight.

This composition gave a pH of about 6.8 and a viscosity of the order of 6,000 CP. In one variation, the fatty acid amides of alkyl betaine were replaced by (dodecyl-hydroxyethyl)-sulphonic-1-sulpho-3 propane which led to a very marked increase in the foaming power.

EXAMPLE 13

To a white glycerophthalic paint, from which the pigments had settled out completely after two months storage, 1.6% of propyl dodecyl sulphoxide were added. After homogenizing the paint and sealing it in an air-tight container, it was allowed to stand at room temperature. There was practically no sedimentation after seven months.

EXAMPLE 14

Three shampoo compositions were prepared with 10 parts by weight of a cationic detergent (tetradecyl dimethyl sulphonium methosulphate) to 87 parts of water. 3 parts by weight of an organic sulphoxide were added to two of them as a reinforcing agent. After homogenization of each of the three compositions, the foaming and wetting properties were determined after dilution to an active matter concentration of 1 gram/liter of water. The viscosity was measured on the undiluted compositions. The results are tabulated below:

|  | COMPOSITION | | |
|---|---|---|---|
|  | I Without Reinforcing Agent | II Decyl-methyl Sulphoxide | III Dodecyl-hydroxy ethyl sulphoxide |
| Foam height in mm: | | | |
| after 30 seconds | 165 | 193 | >187 |
| after 1 minute | 165 | 191 | 187 |
| after 3 minutes | 164 | 191 | 186 |
| after 5 minutes | 162 | 189 | 186 |
| Wetting time in secs | 860 | 386 | 660 |
| Viscosity in CPS at 25° C | 1.56 | 149 | 518 |

These results show that the addition of sulphoxides increases the volume of foam, accelerates wetting and causes a considerable increase in the viscosity of the composition.

EXAMPLE 15

Compositions similar to those of Example 14 were prepared with the amphoteric detergent known under the trade name of "Amphotensid B4" (a fatty acid amino-alkyl betaine).

The following results were then observed:

|  | COMPOSITION | | |
|---|---|---|---|
|  | IV Without Reinforcing Agent | V Decyl-methyl sulphoxide | VI Dodecyl-methyl sulphoxide |
| Foam height in mm: | | | |
| after 30 secs. | 120 | 165 | 146 |
| after 1 min. | 120 | 165 | 146 |
| after 3 mins. | 120 | 165 | 144 |
| after 5 mins. | 115 | 165 | 141 |
| Wetting time in secs | 921 | 201 | 174 |
| Viscosity in CPs at 25° C | 0.88 | 1.86 | 3.75 |

It will be seen observed that with the amphoteric detergent, the addition of the sulphoxide greatly improves the foaming power and the wetting rate. The viscosity is also increased, but to a lesser extent than in Example 14.

While, when applying the invention, various dialkyl-sulphoxides and hydroxy-dialkyl-sulphoxides may be used for improving cosmetic composition, ones which are particularly suitable are those which correspond to the formula $$R^1 - SO - R^2$$

where $R^1$ is a $C_1 - C_4$ alkyl or hydroxy-alkyl, while $R^2$ is a heavier alkyl with 6 to 18 carbon atoms and preferably 8 to 12 carbon atoms.

While it will be apparent that the illustrated embodiments of the invention herein disclosed are well calculated adequately to fulfill the objects and advantages primarily stated, it is to be understood that the invention is susceptible to variation, modification, and change within the spirit and scope of the subjoined claims.

The invention having been thus described, what is claimed as new and desired to secure by Letters Patent is:

1. An improvement in the method of producing organic sulphoxides selected from the group consisting of dialkyl sulphoxides bearing a total of 2 to 36 carbon atoms, their corresponding hydroxy-substituted alkyl sulphoxides and polymethylene sulphoxides having 2 to 6 carbon atoms, by oxidizing a sulfide selected from the group consisting of dialkyl sulfides of formula $R^1-S-R^2$ having a total of 2 to 36 carbon atoms and wherein $R^1$ and $R^2$ are chosen from a group consisting of alkyl and hydroxyalkyl groups, and polymethylene sulfides of formula

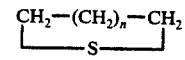

wherein $n$ is an integer of 0 to 4, with hydrogen peroxide in a reaction medium of an aqueous acidic medium and a solvent selected from the group consisting of benzene, toluene, hexane, heptane, dichloroethane, chloroprene, propyl acetate and isobutyl acetate, said solvent forming an azeotropic mixture with between 5 and 20% by weight of water, said solvent having the capacity for dissolving the dialkyl sulfides, while leaving the sulphoxide substantially undissolved at a temperature substantially below the boiling point of said mixture, and separating the sulphoxide formed from the reaction medium by distilling the azeotropic mixture from the solvent after the oxidation has been effectuated and allowing said medium to cool to the point where a precipitation of sulphoxide is formed.

2. An improvement as recited in claim 1, wherein the solvent is hexane.

3. An improvement as recited in claim 1, wherein the solvent is heptane.

* * * * *